["United States Patent" [19]]

McAlpine et al.

[11] 4,223,024
[45] Sep. 16, 1980

[54] 4"-O-ALKYLGENTAMICINS AND SAGAMICINS

[75] Inventors: James B. McAlpine; Robert L. DeVault, both of Libertyville, Ill.

[73] Assignee: Abbott Laboratories, North Chicago, Ill.

[21] Appl. No.: 19,982

[22] Filed: Mar. 12, 1979

[51] Int. Cl.$^2$ ...................... A61K 31/71; C07H 15/22
[52] U.S. Cl. .................................. 424/180; 536/17 R
[58] Field of Search ........................... 536/17; 424/180

[56] References Cited

U.S. PATENT DOCUMENTS

| | | | |
|---|---|---|---|
| 4,044,123 | 8/1977 | Daniels et al. | 536/17 |
| 4,055,715 | 10/1977 | Tomioka et al. | 536/17 |

Primary Examiner—Johnnie R. Brown
Attorney, Agent, or Firm—Robert L. Niblack; Gildo E. Fato; Joyce R. Niblack

[57] ABSTRACT

4"-O-alkylgentamicins and sagamicins represented by the formula:

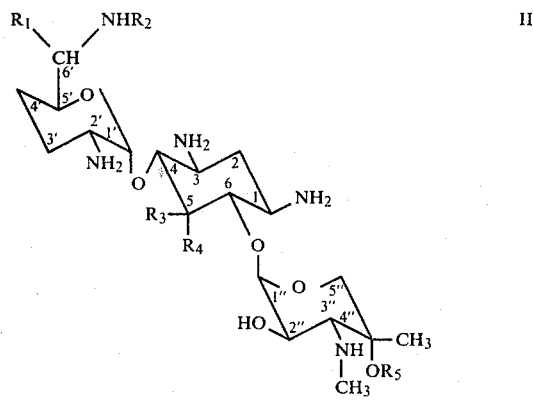

wherein $R_1$ is hydrogen or methyl: $R_2$ is hydrogen or methyl; $R_3$ is hydrogen or hydroxy; $R_4$ is hydroxy when $R_3$ is hydrogen and hydrogen when $R_3$ is hydroxy; and $R_5$ is loweralkyl; and the pharmaceutically acceptable salts thereof, intermediates therefor, and compositions and methods employing the potent antibiotics of this invention.

44 Claims, No Drawings

4''-O-ALKYLGENTAMICINS AND SAGAMICINS

BACKGROUND OF THE INVENTION

Gentamicin is one of the aminoglycoside antibiotics which have their greatest utility in treating infections caused by gram-negative aerobic bacteria. (See, for example Barza et al., *Am. J. Hosp. Pharm.* 34: 723–737 (July, 1977). While gentamicin is effective against most aerobic gram-negative bacteria, resistance is increasing and some strains of Proteus, Klebsiella, Serratia and Pseudomonas aeruginosa have become resistant to gentamicin therapy. (Barza et al., supra, p. 725).

Gentamicin sulfate (Garamycin) was the most widely prescribed parenteral aminoglycoside antibiotic in 1977, but the spread of gentamicin-resistant organisms has reduced its efficacy against gram negative bacilli. (Rahal, Jr., *Current Prescribing,* pp. 30–35 (August, 1977). Thus, while gentamicin is a valuable therapeutic tool in the fight against infections caused by aerobic gram-negative bacteria, the need for new gentamicin derivatives which exhibit activity against gentamicin-resistant strains has existed for several years.

Sagamicin is a structurally related aminoglycoside antibiotic which exhibits a similar anti-bacterial spectrum to that of gentamicin and further exhibits lower ototoxicity than does gentamicin.

The present invention provides new derivatives of gentamicin and sagamicin.

SUMMARY

The present invention provides new derivatives of gentamicins and sagamicin, and specifically provides 4''-O-alkyl derivatives of gentamicin $C_{1a}$, gentamicin $C_2$, gentamicin $C_1$ and sagamicin.

The above antibiotics are represented by formula I as follows:

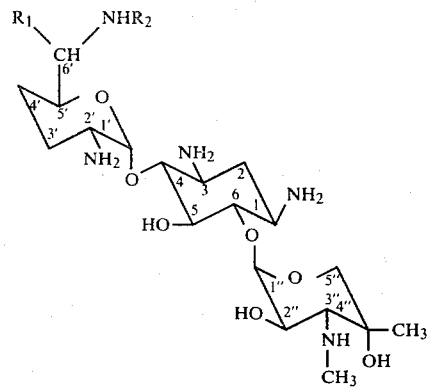

wherein $R_1$ and $R_2$ have the following values for the above antibiotics:

| $R_1$ | $R_2$ | Antibiotic |
|---|---|---|
| H | H | gentamicin $C_{1a}$ |
| $CH_3$ | H | gentamicin $C_2$ |
| $CH_3$ | $CH_3$ | gentamicin $C_1$ |
| H | $CH_3$ | sagamicin |

The 4''-O-alkyl derivatives of the above aminoglycoside antibiotics are extremely potent antibiotics which are effective against susceptible gram-postive and gram-negative bacilli such as *Staphyloccocus aureus, Streptococcus faecalis Escherichia coli, Pseudomonas aeruginosa, Bacillis subtilis, Proteus vulgaris, Shigella sonnei, Salmonella typhi,* and *Klebsiella pneumonia.*

DETAILED DESCRIPTION OF THE PREFERRED EMBODIMENTS

The present invention provides highly potent gentamicin and sagamicin derivatives, specifically, 4''-O-loweralkyl derivatives of gentamicins and sagamicin represented by Formula II:

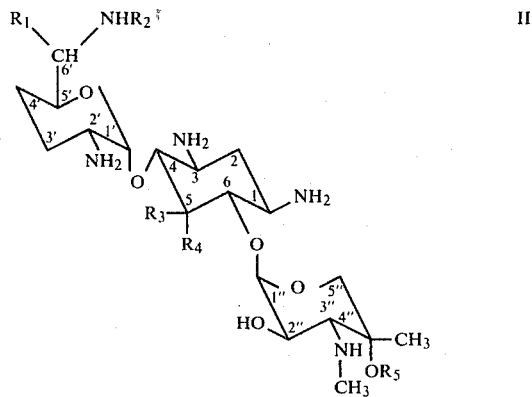

wherein $R_1$ is hydrogen or methyl; $R_2$ is hydrogen or methyl; $R_3$ is hydrogen or hydroxy; $R_4$ is hydroxy when $R_3$ is hydrogen and hydrogen when $R_3$ is hydroxy; and $R_5$ is loweralkyl; and the pharmaceutically acceptable salts thereof.

The term "loweralkyl", as used herein, refers to straight or branched chain alkyl radicals containing from 1 to 6 carbon atoms including but not limited to methyl, ethyl, n-propyl, iso-propyl, n-butyl, sec-butyl, 2-methyhexyl, n-pentyl, 1-methylbutyl, 2,2-dimethylbutyl, 2-methylpentyl, 2,2-dimethylpropyl, n-hexyl and the like.

The term "pharmaceutically acceptable salts" refers to non-toxic acid addition salts of the compounds of Formula II which are generally prepared by reacting the free base with a suitable organic or inorganic acid. Representative salts include the mono, di, tri, tetra or penta-hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tatrate, napsylate, and like salts.

The aminoglycoside antibiotics of Formula II are potent antibacterial agents which are effective against sensitive or susceptible strains of gram-negative and gram-positive bacilli such as *Staphylococcus aureus, Streptococcus faecalis, Escherichia coli, Pseudomonas aeruginosa, Bacillus subtilis, Proteus vulgaris, Shigella sonnei, Salmonella typhi* and *Klebsiella pneumoniae.* The antibiotics of this invention are administered parenterally, i.e. intravenously, intramuscularly, intraperitoneally, or subcutaneously for systemic effect in daily dosages of from 2–10 mg/kg of body weight daily, and preferably from 4–6 mg/kg of body weight daily, based on lean body weight as is good medical practice with the aminoglycoside antibiotics.

The compounds can also be administered orally at the above dosages to sterilize the intestinal tract, and can further be administered in suppository form.

The term "susceptible or sensitive strains" refers to strains of organisms which have demonstrated to be sensitive to a particular antibiotic in a standard in vitro sensitivity test and thus in vitro activity of an antibiotic against a specific strain of a specific bacillus has been established.

The presently preferred 4''-O-loweralkyl derivatives of this invention are the 4''-O-methyl derivatives.

The present invention also provides intermediates which are useful in the preparation of the antibiotics of Formula II. The intermediates fall into two classes, and are set forth in the following description of the intermediates as compounds of Formula III and compounds of Formula IV.

In the following formulae, $R_1$, $R_2$, $R_3$, $R_4$ and $R_5$ are as defined in Formula II, supra. The compounds of Formula III are per-N-protected intermediates and the compounds of Formula IV are cyclicureides.

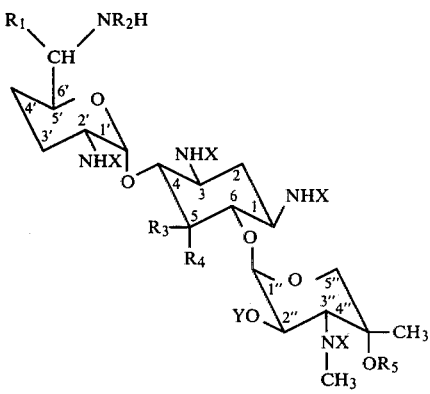

wherein: $R_1$ is hydrogen or methyl; $R_2$ is hydrogen or methyl; X is $R_6CO-$ wherein $R_6$ is loweralkyl, loweralkoxy or hydrogen; Y is $R_7CO-$ wherein $R_7$ is loweralkyl or hydrogen; $R_3$ and $R_4$ are as defined in Formula II or taken together are oxo and $R_5$ is $-CH_2SCH_3$, $C_8C_9SCHR_8R_9$ or loweralkyl wherein $R_8$ and $R_9$ are loweralkyl or hydrogen.

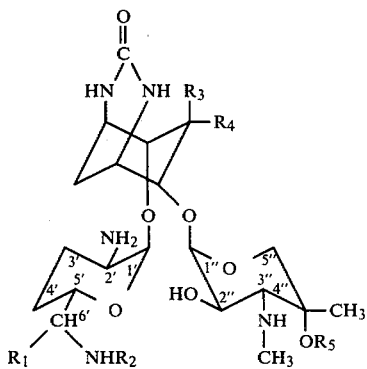

wherein $R_1$, $R_2$, $R_3$, $R_4$ and $R_5$ are as defined in Formula II.

The following examples further illustrate the present invention by illustrating the preparation of representative compounds of this invention.

EXAMPLE 1

Penta-N-5,2''-di-O-acetylgentamicin $C_{1a}$

Gentamicin $C_{1a}$ sulfate (300 mg) in water is passed through a column of Dowex AG 1x2 ion exchange resin(OH form), and washed with five bed-volumes of water and solvent is removed from the eluate. The residue is digested in pyridine (5 ml) and treated with acetic anhydride (2 ml) at 97° C. for three hours. Reagents are removed in vacuo and the crude product purified by chromatography on a column of silica gel eluted with a gradient from chloroform (mixing chamber) to methanol (reservoir). Later fractions are combined and concentrated to yield the desired product (192 mg) as a white glass. The carbon magnetic resonance spectrum is set forth in Table I.

EXAMPLE 2

Penta-N-5,2''-di-O-acetyl-4''-O-methylthiomethylgentamicin $C_{1a}$

Penta-N-5,2''-di-O-acetylgentamicin $C_{1a}$ (202 mg), prepared according to the method of Example 1, is allowed to stand in dimethylsulfoxide (10 ml) and acetic anhydride (5 ml) for 64 hours. Solvents are removed in vacuo and the residue is chromatographed on a column of E.M. Merck silica gel developed with a gradient from chloroform (mixing chamber) to methanol (reservoir). Fractions containing the major component are combined and concentrated to yield the desired product (125 mg) as a white glass. The carbon magnetic resonance spectrum is set forth in Table I.

Example 3

Penta-N-5,2''-di-O-acetyl-4''-O-methylgentamicin $C_{1a}$

Penta-N-5,2''-di-O-acetyl-4''-O-methylthiomethylgentamicin $C_{1a}$ (125 mg) and Raney Nickel (about 5 g) in ethanol (50 ml) are heated under reflux for 3½ hours. The mixture is cooled and filtered through a pad of celite. The residues are washed well with methanol and the combined filtrate and washings are concentrated to a residue of crude product (79 mg). Chromatography over a column of silica gel eluted with a gradient from chloroform (mixing chamber) to chloroform-methanol (1:1 v/v) (reservoir) affords penta-N-5,2''-di-O-acetyl-4''-O-methylgentamicin $C_{1a}$ (34 mg) as a white glass. $R_f$ 0.23. TLC analytical silica gel plates are developed with chloroform-methanol (1:1 v/v). The carbon magnetic resonance spectrum is set forth in Table I.

EXAMPLE 4

4''-O-Methylgentamicin $C_{1a}$

Penta-N-5,2''-di-O-acetyl-4''-O-methylgentamicin $C_{1a}$ (34 mg) in water (20 ml) is treated with barium hydroxide octahydrate (500 mg) and heated under reflux for three days. The cooled solution is saturated with carbon dioxide and filtered through a pad of celite. Solvent is removed from the filtrate and the residue is digested in the lower phase of a mixture of equal volumes of chloroform, methanol and concentrated ammonium hydroxide and chromatographed on a column of silica gel developed with the same solvent. Fractions containing the major component are combined and concentrated to yield 4''-O-methylgentamicin $C_{1a}$ (10 mg) as a colorless glass. The carbon magnetic resonance spectrum is set forth in Table I.

EXAMPLE 5

Penta-N-carboethoxysagamicin

Sagamicin sulfate (2.2 g) in water (20 ml) is passed through a column of Dowex AG 1×7 ion exchange resin (OH form) and the column washed with five bed volumes of water. The eluates are concentrated and sodium carbonate (4 g) added. The solution is cooled in an ice bath and stirred during the addition of a solution of ethylchloroformate (4 ml) in acetone (30 ml) over a two hour period. The mixture is poured into water (300 ml) and the resulting solution is extracted with chloroform (5×10 ml). The combined chloroform extracts are washed once with water and concentrated to yield a white glassy residue of the above-named product (2.3 g). The carbon magnetic resonance spectrum is set forth in Table I.

EXAMPLE 6

5,2"-Di-O-acetylpenta-N-carboethoxysagamycin

Penta-N-carboethoxysagamicin (650 mg) in pyridine (20 ml) and acetic anhydride (10 ml) is heated on a boiling water bath for 4 hours and then poured into water (200 ml). The solution is extracted with chloroform (4×50 ml) and the combined extracts are washed with water and concentrated. The residue is freed of reagents by several additions and removals of heptane-methanol mixtures. The crude product is purified by chromatography over Sephadex LH-20 ® gel in methanol to yield the desired product as a white glass (642 mg). The carbon magnetic resonance spectrum is set forth in Table I.

EXAMPLE 7

5,2"-Di-O-acetyl-penta-N-carboethoxy-4"-O-methylsagamicin 5,2"-Di-O-acetyl-penta-N-carboethoxysagamicin (640 mg) in dimethylsulfoxide (40 ml) and acetic anhydride (15 ml) is allowed to stand at room temperature for three days. Solvents are removed in vacuo and the oily residue is digested in ethanol (50 ml), treated with Raney Nickel (about 10 g) and heated under reflux 2½ hours. The cooled mixture is filtered through a pad of celite and the pad is washed well with methanol. The combined filtrates and washings are concentrated and the residue is chromatographed over a column of silica gel eluted with a gradient from chloroform (mixing chamber) to chloroform-methanol (3:1 v/v) (reservoir). Early fractions are combined and concentrated to yield 507 mg of product as a white glass. The carbon magnetic resonance spectrum is set forth in Table I.

EXAMPLE 8

4"-O-Methylsagamicin and 4"-O-methylsagamicin-1N,3N-cyclicureide 5,2"-di-O-acetylpenta-N-carboethoxy-4"-O-methyl-sagamicin (205 mg) in water (5 ml) are treated with barium hydrochloride octahydrate (5 g) and heated under reflux for two days. The cooled mixture is filtered through a pad of celite which is then washed well with methanol. Solvent is removed from the washed filtrate and washings. The residue is digested in the lower phase of a mixture of equal volumes of chloroform-methanol-concentrated ammonium hydroxide and chromatographed over a column of silica gel developed with the same solvent system. Initial fractions are combined and concentrated to give 26 mg of the 4"-O-methysagamicin as a white glass. Later fractions are combined and concentrated to yield 4"-O-methylsagamicin-1N,3N-cyclicureide (35 mg) as a white glass. The carbon magnetic resonance spectra are set forth in Table I.

EXAMPLE 9

Penta-N-carboethoxygentamicin $C_{1a}$

Gentamicin $C_{1a}$ sulfate (268 g) in water (20 ml) is passed through a column of Dowex AG 1×2 resin (OH⁻ form) and the column is washed with five bed volumes of water. The combined eluates and washings are concentrated, sodium carbonate (5 g) is added to the concentrate, followed by a solution of ethylchloroformate (5 ml) in acetone (25 ml). The mixture is stirred for two hours and then poured into water (200 ml). The mixture is extracted with chloroform (4×50 ml) and the combined extracts are concentrated to yield penta-N-carboethoxygentamicin $C_{1a}$ (2.78 g). This is purified by chromatography over a column of silica gel developed with a gradient from chloroform (750 ml, mixing chamber) and chloroform (600 ml)methanol (150 ml) (reservoir). Fractions containing the major component are combined and concentrated to yield 249 g of product as a white glass. The carbon magnetic resonance spectrum is set forth in Table I.

EXAMPLE 10

2"-O-Acetylpenta-N-carboethoxygentamicin $C_{1a}$

Penta-N-carboethoxygentamicin $C_{1a}$ (520 ml) in pyridine (10 ml) is treated with acetic anhydride (2 ml) and allowed to stand at room temperature for 5 hours. Reagents are removed under vacuum and the oily residue is digested in chloroform and chromatographed over a column of silica gel eluted with a gradient from chloroform (mixing chamber) to methanol (reservoir). Fractions containing the major components are combined and concentrated to yield 2"-O-acetylpenta-N-carboethoxygentamicin $C_{1a}$ (340 g) as a white glass. The carbon magnetic resonance spectrum is set forth in Table I.

EXAMPLE 11

2"-O-Acetyl-5-epi-4"-O-methylpenta-N-ethoxycarbonylgentamicin $C_{1a}$

2"-O-Acetylpenta-N-carboethoxygentamicin $C_{1a}$ (300 mg) in dimethylsulfoxide (20 ml) and acetic anhydride (10 ml) is allowed to stand at room temperature for two days. Solvents are removed in vacuo and the oily residue is digested in ethanol (50 ml), treated with Raney Nickel (7 g) and heated under reflux for 3 hours. The cooled mixture is filtered through a pad of celite and the pad is washed well with methanol. Solvent is removed from the combined filtrate and washings and the residue is chromatographed over a column of silica gel eluted with a gradient from chloroform (mixing chamber) to methanol (reservoir). Fractions containing the major component are combined and concentrated to yield 253 mg of the desired product as a white glass. The carbon magnetic resonance spectrum is set forth in Table I.

EXAMPLE 12

5-Epi-4"-O-methylgentamicin $C_{1a}$ and 5-epi-4"-O-methylgentamicin $C_{1a}$-1N,3N-cyclic ureide 2"-O-acetyl-5-epi-4"-O-methylpenta-N-ethoxycarbonylgentamicin $C_{1a}$ (200 mg) in water (50 ml) is treated with barium hydroxide octahydrate (5 g) and heated under reflux for seven days. The cooled mixture is filtered through a pad of celite which is then washed well with methanol. Solvent is removed from the combined filtrate and washing and the residue is chromatographed on a column of silica gel eluted with the lower phase of a mixture of equal volumes of methanol, chloroform and concentrated ammonium hydroxide. Fractions containing like components are combined and concentrated to yield 5-epi-4''-O-methylgentamicin $C_{1a}$ (15 mg) and 5-epi-4''-O-methylgentamicin $C_{1a}$-1N,3N-cyclic ureide (55 mg) as a white glass. The carbon magnetic resonance spectra are set forth in Table I.

EXAMPLE 13

Penta-N-5,2''-di-O-acetylgentamicin $C_1$

Gentamicin $C_1$ sulfate (300 mg) in water is passed through a column of Dowex AG 1×2 ion exchange resin (OH form) washed with five bed-volumes of water and solvent is removed from the eluate. The residue is digested in pyridine (5 ml) and treated with acetic anhydride (2 ml) at 97° C. for three hours. Reagents are removed in vacuo and the crude product purified by chromatography on a column of silica gel eluted with a gradient from chloroform (mixing chamber) to methanol (reservoir). Later fractions are combined and concentrated to yield the desired product.

EXAMPLE 14

Penta-N-5,2''-di-O-acetyl-4''-O-methylthiomethylgentamicin $C_1$

Penta-N-5,2''-di-O-acetylgentamicin $C_1$ (200 mg), prepared according to the method of Example 13, is allowed to stand in dimethylsulfoxide (10 ml) and acetic anhydride (5 ml) for 64 hours. Solvents are removed in vacuo and the residue is chromatographed on a column of E.M. Merck silica gel developed with a gradient from chloroform (mixing chamber) to methanol (reservoir). Fractions containing the major component are combined and concentrated to obtain the desired product.

EXAMPLE 15

Penta-N-5,2''-di-O-acetyl-4''-O-methylgentamicin $C_1$

Penta-N-5,2''-di-O-acetyl-4''-O-methylthiomethylgentamicin $C_1$ (125 mg) and Raney Nickel (ca 5 g) in ethanol (50 ml) are heated under reflux for 3½ hours. The mixture is cooled and filtered through a pad of celite. The residues are washed well with methanol and the combined filtrate and washings are concentrated to a residue of crude product. Chromatography over a column of silica gel eluted with a gradient from chloroform (mixing chamber) to methanol-chloroform (1:1 v/v) (reservoir) affords the desired product.

EXAMPLE 16

4''-O-Methylgentamicin $C_1$

The compound of Example 15 (34 mg) in water (20 ml) is treated with barium hydroxide octahydrate (500 mg) and heated under reflux for three days. The cooled solution is saturated with carbon dioxide and filtered through a pad of celite. Solvent is removed from the filtrate and the residue is digested in the lower phase of a mixture of equal volumes of chloroform, methanol and concentrated ammonium hydroxide and chromatographed on a column of silica gel developed with the same solvent. Fractions containing the major component are combined and concentrated to yield the desired product.

EXAMPLE 17

Penta-N-5,2''-di-O-acetylgentamicin $C_2$

Gentamicin $C_2$ sulfate (300 mg) in water is passed through a column of Dowex AG 1×2 ion exchange resin (OH$^-$ form) and washed with five bed-volumes of water and solvent is removed from the eluate. The residue is digested in pyridine (5 ml) and treated with acetic anhydride (2 ml) at 97° C. for three hours. Reagents are removed in vacuo and the crude product purified by chromatography on a column of silica gel eluted with a gradient from chloroform (mixing chamber) to methanol (reservoir). Later fractions are combined and concentrated to yield the desired product.

EXAMPLE 18

Penta-N-5,2''-di-O-acetyl-4''-O-methylthiomethylgentamicin $C_2$

Penta-N-5,2''-di-O-acetylgentamicin $C_2$ (200 mg) is allowed to stand in dimethylsulfoxide (10 ml) and acetic anhydride (5 ml) for 64 hours. Solvents are removed in vacuo and the residue is chromatographed on a column of E.M. Merck silica gel developed as described in Example 14. Fractions containing the major component are combined and concentrated to obtain the desired product.

EXAMPLE 19

Penta-N-5,2''-di-O-acetyl-4''-O-methylgentamicin $C_2$

The compound of Example 18 (125 mg), Raney Nickel (5 mg) and ethanol (50 ml) are heated under reflux for 3½ hours and filtered through a pad of celite. The residues are washed well with methanol and the combined filtrate and washings are concentrated to a residue of crude product. Chromatography over a column of silica gel eluted with a gradient from chloroform (mixing chamber) to methanol-chloroform (1:1 v/v) (reservoir) affords the desired product.

EXAMPLE 20

4''-O-Methylgentamicin $C_2$

The compound of Example 19 (34 mg) in water (20 ml) is treated with barium hydroxide octahydrate (500 mg) and heated under reflux for three days. The cooled solution is saturated with carbon dioxide and filtered through a pad of celite. Solvent is removed from the filtrate and the residue is digested in the lower phase of a mixture of equal volumes of chloroform, methanol and concentrated ammonium hydroxide and chromatographed on a column of silica gel developed with the same solvent. Fractions containing the major component are combined and concentrated to yield the desired product.

Sagamicin can be prepared as described by R. Okachi et al., *J. Antibiotics*, 27, pp. 793–800 (October, 1974). The Okachi et al. article is entitled "A New Antibiotic XK-62-2 (Sagamicin) 1. Isolation, Physiochemical and Antibacterial Properties"

The synethesis of the gentamicin mixture is disclosed in U.S. Pat. No. 3,091,572 and the separation of the compounds gentamicin $C_1$, gentamicin $C_{1a}$ and gentamicin $C_2$ is disclosed in U.S. Pat. No. 3,651,042.

The carbon magnetic resonance spectra for the compounds of the preceeding examples is set forth in the following Table I.

TABLE I

| | Example 1 | Example 2 | Example 3 | Example 4 | Example 5 | Example 6 | Example 7 | Example 8 Cpd. 1 | Example 8 Cpd. 2 | Example 9 | Example 10 | Example 12 |
|---|---|---|---|---|---|---|---|---|---|---|---|---|
| $C_1'$ | 99.4 | 96.5 | 98.0 | 101.9 | 98.4 | 96.6 | 96.4 | 101.3 | 100.4 | 98.3 | 98.3 | 102.3 |
| $C_2'$ | 49.8 | 48.9 | 49.7 | 50.8 | 50.3 | 50.0 | 56.2 | 50.5 | 50.3 | 50.2 | 50.2 | 50.3 |
| $C_3'$ | 23.5 | 23.0 | 23.4 | 26.9 | 24.0 | 23.7 | 23.8 | 26.5 | 27.0 | 23.9 | 23.9 | 27.2 |
| $C_4'$ | 27.7 | 27.8 | 27.7 | 28.3 | 27.3 | 27.5 | 27.5 | 28.6 | 28.5 | 27.5 | 27.4 | 28.3 |
| $C_5'$ | 68.1 | 67.8 | 68.0 | 71.2 | 67.2 | 67.2 | 67.3 | 68.3 | 68.2 | 67.1 | 67.2 | 70.7 |
| $C_6'$ | 43.9 | 43.8 | 43.8 | 45.9 | 51.9 | 52.1 | 52.1 | 55.1 | 54.9 | 45.0 | 45.0 | 45.7 |
| $NCH_3$ | | | | | 35.3 | 35.5 | 35.5 | 35.3 | 35.2 | | | |
| $C_1$ | 49.4 | 48.4 | 48.5 | 51.5 | 50.9 | 51.3 | 51.4 | 51.5 | 47.9 | 50.8 | 50.9 | 48.2 |
| $C_2$ | 32.9 | 33.2 | 33.0 | 36.6 | 30.0 | 30.0 | 30.2 | 36.5 | 18.2 | 30.0 | 30.0 | 36.7 |
| $C_3$ | 49.0 | 48.4 | 48.5 | 50.4 | 50.1 | 50.0 | 50.2 | 50.3 | 45.9 | 50.2 | 50.0 | 47.5 |
| $C_4$ | 81.2 | 81.4 | 81.4 | 87.9 | 82.3 | 77.6 | 77.7 | 87.6 | 78.7 | 82.4 | 82.4 | 85.8 |
| $C_5$ | 76.2 | 77.5 | 77.6 | 75.3 | 74.8 | 76.5 | 76.5 | 75.3 | 69.3 | 74.9 | 74.9 | 68.7 |
| $C_6$ | 79.8 | 80.4 | 80.1 | 86.6 | 82.1 | 76.5 | 76.5 | 87.0 | 77.9 | 81.8 | 82.1 | 79.6 |
| $C_1''$ | 97.6 | 96.5 | 96.5 | 101.0 | 98.8 | 96.4 | 96.4 | 101.0 | 98.8 | 98.8 | 96.3 | 96.2 |
| $C_2''$ | 65.2 | 63.7 | 65.1 | 70.0 | 64.5 | 66.4 | 65.9 | 69.9 | 70.5 | 64.5 | 66.3 | 70.1 |
| $C_3''$ | 56.5 | 54.4 | 56.3 | 62.2 | 58.5 | 55.5 | 56.3 | 62.0 | 62.1 | 58.5 | 55.4 | 62.0 |
| $C_4''$ | 74.7 | 75.3 | 75.1 | 77.7 | 73.1 | 73.1 | 78.3 | 77.7 | 77.5 | 73.1 | 73.1 | 77.7 |
| $C_5''$ | 69.8 | 75.0 | 66.1 | 65.3 | 69.6 | 69.0 | 61.7 | 65.2 | 65.6 | 69.6 | 69.0 | 65.1 |
| $CCH_3$ | 23.0 | 17.1 | 17.2 | 17.4 | 22.2 | 22.0 | 16.1 | 17.3 | 17.4 | 22.2 | 22.1 | 17.3 |
| $NCH_3$ | 33.8 | 33.8 | 33.8 | 33.8 | 34.6 | 34.7 | 34.8 | 37.9 | 38.3 | 34.7 | 34.7 | 38.0 |
| $OCH_3$ | | | 48.9 | 49.7 | | | 48.6 | 49.7 | 49.7 | | | 49.7 |
| $SCH_3$ | | 14.6 | | | | | | | | | | |
| $S-CH_2O$ | | 63.7 | | | | | | | | | | |
| Cbe | | | | | 14.5 | 14.5 | 14.5 | | | 14.5 | 14.5 | |
| | | | | | 59.6 | 59.7 | 59.8 | | | 59.7 | 59.8 | |
| | | | | | 60.4 | 59.9 | 60.0 | | | 60.5 | 60.0 | |
| | | | | | 60.6 | 60.6 | 60.7 | | | 155.7 | 60.5 | |
| | | | | | 156.1 | 155.6 | 60.8 | | | 156.1 | 155.9 | |
| | | | | | 155.7 | 155.8 | 155.5 | | | 156.5 | 156.3 | |
| | | | | | | 156.2 | 155.6 | | | | 156.7 | |
| | | | | | | 156.9 | 155.7 | | | | | |
| Ac | 21.5 | 21.2 | 21.4 | | | 20.5 | 20.5 | | | 21.3 | | |
| | 22.2 | 22.1 | 22.2 | | | 21.2 | 21.2 | | | 170.0 | | |
| | 22.7 | 22.8 | 22.7 | | | 169.2 | 169.3 | | | | | |
| | 174.1 | 23.0 | 174.0 | | | 169.7 | 169.8 | | | | | |
| | 174.6 | 173.7 | 175.1 | | | | | | | | | |
| | 175.1 | 174.0 | 176.9 | | | | | | | | | |
| | 177.1 | 175.0 | | | | | | | | | | |
| | | 176.8 | | | | | | | | | | |
| C=O | | | | | | | | | 159.2 | | | |

Spectra of Examples 1,2,3,4 8 (both compounds) and 12 were determined in deuterium oxide at ambient temperature. Those of examples 5,6,7,9 and 10 were determined in perdeuterodimethylsulfoxide at 100° C. Assisgnments are made from analogy with other known gentamicin derivatives and with consideration for the known effects of structural change on carbon magnetic resonance spectra. Interchange of assignments of resonances of similar chemical shift can be made without affecting the characterization of the compounds or the structural inferences of the spectra.

The in vitro antibiotic activity is determined by a two fold dilution test using Streptomycin Assay Agar with yeast extract (at pH 7.9). The inoculum of approximately $1 \times 10^5$ of the indicated test organism is delivered by a multiple inoculator. The test is incubated over night.

The minimum inhibitory concentrations for the compounds of Example 4, Example 8, compound 1 and Example 12 compound, are set forth in Table II. The minimum inhibitory concentrations (MIC) are expressed in micrograms per ml.

Table II

| | MIC (mcg/ml.) | | |
|---|---|---|---|
| Organism | Ex 4. | Ex 8(1) | Ex 12 |
| Staphylococcus aureus ATCC 6538P | 0.005 | 0.05 | 0.005 |
| Streptococcus faecalis ATCC 10541 | 10.000 | 12.5 | 25.00 |
| Escherichia coli ATCC 26 | 0.005 | 0.05 | 0.02 |
| Escherichia coli R3 | 10.000 | 3.1 | 2.5 |
| Pseudomonas aeruginosa BMH #1 | 0.63 | 0.4 | 0.63 |
| Bacillis subtilis U. of Il. 10707 | 0.005 | 0.005 | 0.005 |
| Proteus vulgaris ATCC 6897 | 0.08 | 0.05 | 0.08 |
| Shigella sonnei ATCC 9290 | 0.04 | 0.05 | 0.08 |
| Salmonella typhi ATCC 9992 | 0.01 | 0.05 | 0.01 |
| Klebsiella pneumonia ATCC 10031 | 0.005 | 0.05 | 0.005 |

The compounds of formula II are active as systemic antibiotics when administered by parenteral routes of administration as discussed hereinabove. They can be administered by the intramuscular, intravenous, intraperitoneal or subcutaneous routes of administration in daily dosages of from 2 to 10 mg/kg, preferably in divided dosages based on lean body weight. The compounds can also be adminstered orally to sterilize the intestinal tract and additionally can be applied topically or administered as rectal suppositories.

Preparations of this invention for parenteral administration include sterile aqueous or non-aqueous solutions, suspensions or emulsions. Examples of suitable non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the composition, etc. They can be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

Solid dosage forms for oral administration include tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g, lubricating agents such as magnesium stearate. In the case of capsules, tablets and pills, the dosage forms may also comprise buffering agents. Tablets and pills can additionally be prepared with enteric coatings to ensure the antibiotic reaches the intestinal tract.

Liquid dosage forms for oral administration include pharmaceutically acceptable emulsions, solutions, suspensions, syrups and elixirs containing inert diluents commonly used in the art such as water. Besides such inert diluents, the liquid compositions can also include adjuvants such as wetting agents, emulsifying agents and suspending agents, as well as sweetening, flavoring and perfuming agents.

It will be readily apparent to those skilled in the art that the 4″-O-alkyl-gentamicins and sagamicins of this invention when the alkyl is other than methyl can be prepared according to the methods of the examples, substituting the appropriate dialkyl sulfoxide as the reagent in a reaction such as that described in example 2,7,11,14 or 18. For example, the use of tetrahydrothiophene sulfoxide will result in the preparation of 4″-O-n-butylgentamicins or sagamicin.

When $R_5$ is a tertiary loweralkyl radical, alkylation is affaceted by conventional means, not the route described herein.

We claim:

1. A compound selected from the group consisting of a 4″-O-alkylgentamicin and 4″-O-alkyl-sagamicin represented by the formula:

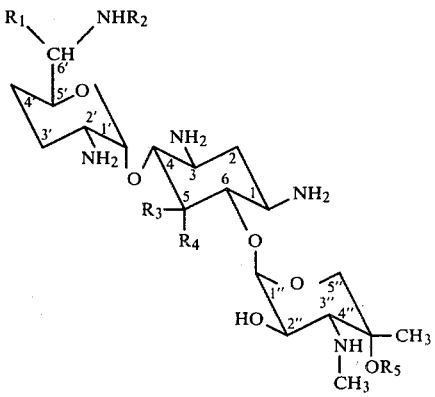

wherein $R_1$ is hydrogen or methyl: $R_2$ is hydrogen or methyl; $R_3$ is hydrogen or hydroxy; $R_4$ is hydroxy when $R_3$ is hydrogen and hydrogen when $R_3$ is hydroxy; and $R_5$ is loweralkyl; and the pharmaceutically acceptable salts thereof.

2. A compound of claim 1 wherein $R_1$ and $R_2$ each are hydrogen.

3. A compound of claim 2: 4″-O-methylgentamicin $C_{1a}$ or a pharmaceutically acceptable salt thereof.

4. A compound of claim 2: 4″-O-ethylgentamicin $C_{1a}$ or a pharmceutically acceptable salt thereof.

5. A compound of claim 2: 4″-O-n-propylgentamicin $C_{1a}$ or a pharmaceutically acceptable salt thereof.

6. A compound of claim 2: 4″-O-iso-propylgentamicin $C_{1a}$ or a pharmaceutically acceptable salt thereof.

7. A compound of claim 2: 4″-O-n-butylgentamicin $C_{1a}$ or a pharmaceutically acceptable salt thereof.

8. A compound of claim 2: 4″-O-sec-butylgentamicin $C_{1a}$ or a pharmaceutically acceptable salt thereof.

9. A compound of claim 2: 4″-O-tert-butylgentamicin $C_{1a}$ or a pharmaceutically acceptable salt thereof.

10. A compound of claim 2: 4″-O-n-pentylgentamicin $C_{1a}$ or a pharmaceutically acceptable salt thereof.

11. A compound of claim 2: 4″-O-n-hexylgentamicin $C_{1a}$ or a pharmaceutically acceptable salt thereof.

12. A compound of claim 1 wherein $R_1$ is methyl and $R_2$ is hydrogen.

13. A compound of claim 12: 4″-O-methylgentamicin $C_1$ or a pharmaceutically acceptable salt thereof.

14. A compound of claim 12: 4″-O-ethylgentamicin $C_1$ or a pharmaceutically acceptable salt thereof.

15. A compound of claim 12: 4″-O-n-propylgentamicin $C_1$ or a pharmaceutically acceptable salt thereof.

16. A compound of claim 12: 4″-O-iso-propylgentamicin $C_1$ or a pharmaceutically acceptable salt thereof.

17. A compound of claim 12: 4″-O-n-butylgentamicin $C_1$ or a pharmaceutically acceptable salt thereof.

18. A compound of claim 12: 4″-O-sec-butylgentamicin $C_1$ or a pharmaceutically acceptable salt thereof.

19. A compound of claim 12: 4″-O-tert-butylgentamicin $C_1$ or a pharmaceutically acceptable salt thereof.

20. A compound of claim 12: 4″-O-n-pentylgentamicin $C_1$ or a pharmaceutically acceptable salt thereof.

21. A compound of claim 12: 4″-O-n-hexylgentamicin $C_1$ or a pharmaceutically acceptable salt thereof.

22. A compound of claim 1 wherein $R_1$ is methyl and $R_2$ is methyl.

23. A compound of claim 22: 4″-O-methylgentamicin $C_2$ or a pharmaceutically acceptable salt thereof.

24. A compound of claim 22: 4″-O-ethylgentamicin $C_2$ or a pharmaceutically acceptable salt thereof.

25. A compound of claim 22: 4″-O-n-propylgentamicin $C_2$ or a pharmaceutically acceptable salt thereof.

26. A compound of claim 22: 4″-O-iso-propylgentamicin $C_2$ or a pharmaceutically acceptable salt thereof.

27. A compound of claim 22: 4″-O-n-butylgentamicin $C_2$ or a pharmaceutically acceptable salt thereof.

28. A compound of claim 22: 4″-O-sec-butylgentamicin $C_2$ or a pharmaceutically acceptable salt thereof.

29. A compound of claim 22: 4″-O-tert-butylgentamicin $C_2$ or a pharmaceutically acceptable salt thereof.

30. A compound of claim 22: 4″-O-n-pentylgentamicin $C_2$ or a pharmaceutically acceptable salt thereof.

31. A compound of claim 22: 4″-O-n-hexylgentamicin $C_2$ or a pharmaceutically acceptable salt thereof.

32. A compound of claim 1 wherein $R_1$ is hydrogen and $R_2$ is methyl.

33. A compound of claim 32: 4″-O-methylsagamicin or a pharmaceutically acceptable salt thereof.

34. A compound of claim 33: 4″-O-ethylsagamicin or a pharmaceutically acceptable salt thereof.

35. A compound of claim 33: 4″-O-n-propylsagamicin or a pharmaceutically acceptable salt thereof.

36. A compound of claim 33: 4″-O-iso-propylsagamicin or a pharmaceutically acceptable salt thereof.

37. A compound of claim 33: 4″-O-n-butylsagamicin or a pharmaceutically acceptable salt thereof.

38. A compound of claim 33: 4″-O-sec-butylsagamicin or a pharmaceutically acceptable salt thereof.

39. A compound of claim 33: 4″-O-tert-butylsagamicin or a pharmaceutically acceptable salt thereof.

40. A compound of claim 33: 4″-O-n-pentylsagamicin or a pharmaceutically acceptable salt thereof.

41. A compound of claim 33: 4″-O-n-hexylsagamicin or a pharmaceutically acceptable salt thereof.

42. A compound of the formula:

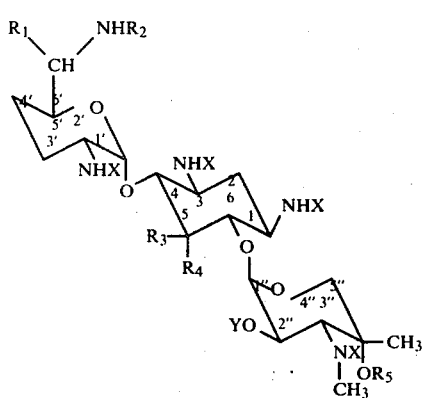

III wherein: $R_1$ is hydrogen or methyl; $R_2$ is hydrogen or methyl; X is $R_6CO$—wherein $R_6$ is loweralkyl, loweralkoxy or hydrogen; Y is $R_7CO$—wherein $R_7$ is loweralkyl or hydrogen; $R_3$ is hydrogen or hydroxy; $R_4$ is hydroxy when $R_3$ is hydrogen and hydrogen when $R_3$ is hydroxy or are taken together to form oxo and $R_5$ is $-CH_2SCH_3$, $C_8C_9SCHR_8R_9$ or loweralkyl wherein $R_8$ and $R_9$ are loweralkyl or hydrogen.

43. A compound of the formula:

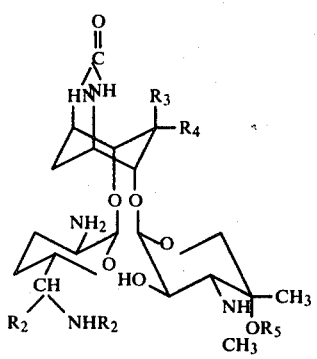

IV wherein $R_1$ is hydrogen or methyl; $R_2$ is hydrogen or methyl; $R_3$ is hydrogen or hydroxy; $R_4$ is hydroxy when $R_3$ is hydrogen and hydrogen when $R_3$ is hydroxy; and $R_5$ is loweralkyl; and the pharmaceutically acceptable salts thereof.

44. A pharmaceutical composition comprising an anti-bacterially effective amount of a compound of claim 1 and a pharmaceutically acceptable carrier or diluent.

* * * * *

UNITED STATES PATENT AND TRADEMARK OFFICE
CERTIFICATE OF CORRECTION

PATENT NO. : 4,223,024
DATED : September 16, 1980
INVENTOR(S) : James B. McAlpine, et. al.

It is certified that error appears in the above-identified patent and that said Letters Patent are hereby corrected as shown below:

In column 14, line 23, at the 6" position, insert a bond between the N and $CH_3$.

Signed and Sealed this

Twenty-third Day of December 1980

[SEAL]

Attest:

SIDNEY A. DIAMOND

Attesting Officer

Commissioner of Patents and Trademarks